(12) United States Patent
Kieran et al.

(10) Patent No.: US 7,897,586 B2
(45) Date of Patent: Mar. 1, 2011

(54) ANAESTHETIC COMPOSITION

(75) Inventors: Peter John Kieran, Nelson's Bay (AU); Kai Kin Lau, Dural (AU); Barry Edward Patten, Panania (AU)

(73) Assignee: Jurox Pty. Ltd., Rutherford (AU)

( * ) Notice: Subject to any disclaimer, the term of this patent is extended or adjusted under 35 U.S.C. 154(b) by 0 days.

(21) Appl. No.: 10/130,573

(22) PCT Filed: Mar. 20, 2001

(86) PCT No.: PCT/AU01/00307
§ 371 (c)(1),
(2), (4) Date: May 17, 2002

(87) PCT Pub. No.: WO01/70234
PCT Pub. Date: Sep. 27, 2001

(65) Prior Publication Data
US 2003/0064961 A1    Apr. 3, 2003

(30) Foreign Application Priority Data
Mar. 20, 2000    (AU) .................................. PQ6339

(51) Int. Cl.
*A61K 31/724*    (2006.01)
(52) U.S. Cl. .......................... 514/58; 514/167
(58) Field of Classification Search ................ 514/171, 514/169; 424/400, 489
See application file for complete search history.

(56) References Cited

U.S. PATENT DOCUMENTS

| 5,324,718 A | 6/1994 | Loftsson |
| 5,472,954 A | 12/1995 | Loftsson |
| 5,935,603 A * | 8/1999 | Derrieu et al. .............. 424/489 |

FOREIGN PATENT DOCUMENTS

| EP | 0 399 716 | * | 5/1990 |
| EP | 0 399 716 A1 | * | 5/1990 |
| EP | 0 399 716 B1 | | 5/1990 |
| WO | PCT/AU93/00100 | | 3/1993 |

OTHER PUBLICATIONS

Development of a Non-Surfactant Formulation for Alfaxalone Through the Use of Chemically-Modified Cyclodextrins by Marcus E. Brewster, Kerry S. Estes, and Nicholas Bodor, Journal of Parenteral Science & Technology, pp. 262-265, 1989.
Parenteral Safety and Uses of 2-Hydroxypropyl B-Cyclodextrin, M.E. Brewster and N. Bodor, pp. 526-534, 1990.
Effect of 2-Hydroxypropyl-Cyclodextrin Complexes of the Neurosteroids, Alfaxalone, Pregnanolone and Pregnenolone, on Various Convulsant Stimuli in the Mousde, M.E. Brewster, W.R. Anderson, T. Loftsson, N. Bodor and E. Pop, pp. 511-514, 1996.
Anesthetic Activity and Pharmacokinetics of the Neurosteroid Alfaxalone Formulated in 2-Hydroxypropyl-Cyclodextrin in the Rat, M.E. Brewster, W.R. Anderson, A. Webb, N. Bodor and E. Pop, pp. 499-502, 1996.
A non-surfactant formulation for alfaxalone based on an amorphous cyclodextrin: Activity studies in rats and dogs, K.S. Estes, M.E. Brewster, A.I. Webb and N. Bodor, 1990, International Journal of Pharmaceutics, 65 (1990) 101-107.

* cited by examiner

*Primary Examiner* — Michael G Hartley
*Assistant Examiner* — Nissa M Westerberg
(74) *Attorney, Agent, or Firm* — SNR Denton US LLP

(57) ABSTRACT

A stable anaesthetic composition is described which is particularly suitable for use in cats and dogs. The composition comprises an aqueous solution of an anaesthetically effective amount of a water soluble cyclodextrin or a cyclodextrin derivative complex of alfaxalone and a buffer, excluding phosphate buffer pH 7.0, 0.1M mixed as defined in the British Pharmacopoeia 1998, such that the pH of the solution is from 6.0-8.0.

12 Claims, No Drawings

ANAESTHETIC COMPOSITION

TECHNICAL FIELD

This invention relates to anaesthetic compositions for use in warm-blooded animals including birds and mammals, reptiles, fish and amphibians and in particular to alfaxalone-based compositions in which the alfaxalone is water-solubilised through the formation of a complex with a cyclodextrin or a cyclodextrin derivative.

BACKGROUND ART

3α-hydroxy-5α-pregnane-11,20-dione (alfaxalone) is a known anaesthetic for use in a variety of animals. Owing to the fact that in use, alfaxalone has a wide safety margin, rapid induction, high potency, absence of nausea and rapid progress to ambulation, it has been regarded as a very useful anaesthetic. However, the substance is quite water insoluble and therefore must be solubilised for effective parenteral use. Solubilisation in saline has been achieved commercially using polyethoxylated castor oil in combination with a small amount of alfadolone acetate (21-acetoxy-3α-hydroxy-5α-pregnane-11,20-dione), a steroid which is half as potent an anaesthetic agent as alfaxalone. Nevertheless, its practical usefulness in mammals has been severely limited since these alfaxalone-based compositions invoke a histamine response in a number of species when administered parenterally.

Because of alfaxalone's efficacy, the present inventors have sought to meet the problem of providing an alfaxalone-based composition which is both anaesthetically effective and able to be administered parenterally to mammals without invoking a histamine response.

It is also evident that for practical reasons it is desirable that formulations of water soluble cyclodextrin or cyclodextrin derivative complexes of alfaxalone are presented as ready-to-use solutions. That is no reconstitution is required prior to use. As used in this specification, "complex" is to be understood as referring to the water soluble moiety formed by the hydrophilic/hydrophobic interaction between alfaxalone and cyclodextrin or cyclodextrin derivative.

It may be expected that owing to the common use of phosphate buffer, 0.1 M mixed pH 7.0 (BP 1998) in parenteral formulations, cyclodextrin or cyclodextrin derivative complexes of alfaxalone-should be suitable for use with this buffer. In fact it has been found by the present inventors that in formulating a ready-to-use anaesthetic composition, there is a fundamental problem in that formulations of the water soluble cyclodextrin or cyclodextrin derivative complexes of alfaxalone with pH 7.0 phosphate buffer are unstable. By unstable it is meant that a crystalline material was formed in a representative formulation within about 7 days when it was stored at 40° C. The presence of such crystals precludes the acceptability in use of such a formulation.

DISCLOSURE OF INVENTION

In seeking to provide a stable ready-to-use formulation of cyclodextrin or cyclodextrin derivative complexes of alfaxalone, the present inventors have established that the nature of the buffer used is important.

Accordingly in a first aspect, the present invention consists in a stable anaesthetic composition which comprises an aqueous solution of an anaesthetically effective amount of a water soluble cyclodextrin or a cyclodextrin derivative complex of alfaxalone and a buffer, excluding phosphate buffer pH 7.0, 0.1 M mixed as defined in the British Pharmacopoeia 1998, such that the pH of the solution is from 4.5-8.0.

In a second aspect, the present invention further consists in a method of anaesthetising warm-blooded animals including birds and mammals, reptiles, fish and amphibians comprising administering to said animals an anaesthetically effective amount of a stable anaesthetic composition which comprises an aqueous solution of an anaesthetically effective amount of a water soluble cyclodextrin or a cyclodextrin derivative complex of alfaxalone and a buffer such that the pH of the solution is from 4.5-8.0.

In a third aspect, the present invention still further consists in a sterile ready-to-use dosage of an anaesthetic comprising a package which includes an aqueous solution of an anaesthetically effective amount of a water soluble cyclodextrin or a cyclodextrin derivative complex of alfaxalone and a buffer, excluding phosphate buffer pH 7.0, 0.1 M mixed as defined in the British Pharmacopoeia 1998, such that the pH of the solution is from 4.5-8.0 and optionally one or more antimicrobial agents.

In a fourth aspect, the present invention provides a sterile dosage of an anaesthetic composition comprising a first package containing in dry form, an anaesthetically effective amount of a water soluble cyclodextrin or a cyclodextrin derivative complex of alfaxalone and a buffer, excluding phosphate buffer pH 7.0, 0.1 M mixed as defined in the British Pharmacopoeia 1998, and a second package of sterile water, the buffer being selected such that a solution formed by dissolving the contents of the first package with contents of the second package has a pH from 4.5-8.0.

In a fifth aspect, the present invention also provides a sterile dosage of an anaesthetic composition comprising a first package containing in dry form, an anaesthetically effective amount of a water soluble cyclodextrin or a cyclodextrin derivative complex of alfaxalone, and a second package containing a sterile aqueous solution of a buffer, excluding phosphate buffer pH 7.0, 0.1 M mixed as defined in the British Pharmacopoeia 1998, the buffer being selected such that a solution formed by dissolving the contents of the first package with contents of the second package has a pH from 4.5-8.0.

In a sixth aspect, the present invention still further provides a sterile dosage of an anaesthetic composition comprising a package containing in dry form for reconstitution with sterile water, an anaesthetically effective amount of a water soluble cyclodextrin or a cyclodextrin derivative complex of alfaxalone and a buffer, excluding phosphate buffer pH 7.0, 0.1 M mixed as defined in the British Pharmacopoeia 1998, and a second package of sterile water, the buffer being selected such that a solution formed by dissolving the contents of the package with sterile water has a pH from 4.5-8.0.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Complexes of alfaxalone with a cyclodextrin or a cyclodextrin derivative may be readily formed by adding an appropriate amount of alfaxalone to a preformed aqueous solution of cyclodextrin or cyclodextrin derivative. Formation of the complex occurs spontaneously which may then be isolated by drying. This process is further described in U.S. Pat. No. 4,727,064. Whilst a variety of cyclodextrins or cyclodextrin derivatives may be used, it is preferred to use 2-hydroxypropyl beta-cyclodextrin as the complexing agent.

Alternatively, the drying step may be omitted. In this case, the requisite amounts of the buffer components are added to the solution of the alfaxalone complex with water being finally added as required to give the desired concentration of alfaxalone in the solution.

A buffer is used in combination with the alfaxalone complex. This buffer must provide a pH for the composition of from 4.5-8.0, preferably 6.0-7.0, most preferably about 6.8.

Whilst a variety of buffer compositions may be used, phosphate-based buffers are preferred, excluding phosphate buffer pH 7.0, 0.1 M mixed (BP 1998). This excluded buffer is formed by dissolving 1.361 g of potassium dihydrogen orthophosphate in sufficient water to produce 100 mL, the pH being adjusted by using a 3.5% w/v solution of disodium hydrogen orthophosphate. Particularly preferred are acid-phosphate buffers, such as citro-phosphate buffer pH 6.5. This buffer is defined in the British Pharmacopoeia 1998 as a mixture of 29.0 mL of 0.1 M citric acid with sufficient 0.2 M anhydrous disodium hydrogen orthophosphate to produce 100 ml. The amount of buffer used relative to the alfaxalone complex may be varied.

In a preferred form, the compositions of the invention are presented in sterile form packed in vials ready-to-use. Whilst in a variety of animals, the compositions will be administered parenterally, in the case of fish, the composition may be mixed in the water containing the fish. In this way, the alfaxalone passes across the gills where it is absorbed systemically to produce the requisite anaesthetic/tranquillising effect. Naturally, the water to which the composition is added will depend on whether the fish are fresh or salt water species.

Other animals that may be effectively anaesthetised with compositions of the invention are mammals including marsupials, sheep, horses, pigs, goats, deer, cattle, dogs and cats. It is particularly useful in dogs as the compositions do not invoke the histamine response of previously known alfaxalone compositions.

The person skilled in the art will appreciate that various antimicrobial agents known in the art may be included in the compositions of the invention to provide an appropriate level of preservation. It will also be appreciated that the compositions of the invention may be sterilised for parenteral use by various methods including autoclaving after being filled into vials or by filtration through a 0.22 µm filter into sterile vials.

The amount of alfaxalone included in a composition will be determined by the nature of the animal to be anaesthetised. For guidance, a level of 1-100 mg/mL, preferably 5-25 mg/mL, most preferably 7-15 mg/mL may be appropriate.

Stability on storage of the compositions of the invention is an important attribute. In general terms, the compositions will have a shelf life of at least 6 months when stored at below 25° C., preferably at least 6 months when stored below 30° C., most preferably at least 2 years when stored below 30° C.

MODES FOR CARRYING OUT THE INVENTION

In order to better understand the nature of this invention, a number of illustrative examples will now be described.

Preparation of Complex

Alfaxalone-Cyclodextrin Powder
1. Add 435 grams of hydroxypropyl-beta cyclodextrin (HPCD) to 1 L of distilled water and stir to dissolve.
2. Add with stirring to the solution 30 g of alfaxalone.
3. Add sufficient dissolved HPCD to adjust the content of alfaxalone to 120 mg per gram of powder when dried.
4. Dry the solution.

Alfaxalone:HPCD Citro-Phosphate Solution
1. Add 435 g of hydroxypropyl-beta cyclodextrin (HPCD) in 1L of water for injection (BP) and stir to dissolve.
2. Add with stirring to the solution 30 g alfaxalone.
3. Add citric acid to the solution from with stirring on the basis of 6.09 g citric acid per L of solution.
4. Add sodium phosphate to the solution with stirring on the basis of 20.08 disodium hydrogen orthophosphate anhydrous per L of solution.
5. Add water for injection (BP) to give a final concentration of alfaxalone of 10 mg/mL.

Determination of Stability

A composition was prepared as described above, filtered through a 0.22µm filter under Class A laminar flow conditions and filled, sealed and capped into clear sterile clear type I glass 13 mL vials with chlorobutyl rubber and aluminium crimp seals. The vials were autoclaved at 121° C. for 20 min with 2 min drying cycle. The composition packed in the vials was subjected to stability testing with the results obtained being set out below in Table 1.

TABLE 1

| TEST | | | | |
|---|---|---|---|---|
| STORAGE CONDITION | TIME | Appearance of the solution | Alfaxalone | pH |
| SPECIFICATION | | Clear Colourless Liquid | 9.0–11 mg/mL | 6.5–7.0 |
| ° C. | Initial | Complies | 9.9 mg/mL | 6.6 |
| 4 | 3 weeks | Complies | 9.9 mg/mL | 6.8 |
| 4 | 7 weeks | Complies | 10.2 mg/mL | 6.7 |
| 4 | 14 weeks | Complies | 10.0 mg/mL | 6.7 |
| 4 | 24 weeks | Complies | 10.09 mg/mL | 6.7 |
| 4 | 36 weeks | Complies | 9.8 mg/mL | 6.7 |
| 4 | 12 months | Complies | 10.0 mg/mL | 6.7 |

Conclusion:

The product is stable following storage at 4° C. for a period of at least 52 weeks with no chemical or physical deterioration evident.

A composition was prepared as described above, filtered through a 0.22 µm filter under Class A laminar flow conditions and filled, sealed and capped into clean sterile clear type I glass 13 mL vials with chlorobutyl rubber and aluminium crimp seals. The composition packed in the vials was subjected to stability testing with the results obtained being set out below in Table 2.

TABLE 2

| TEST | | | | |
|---|---|---|---|---|
| STORAGE CONDITION | TIME (Mths) | Appearance of the solution | Alfaxalone | pH |
| SPECIFICATION | | Clear Colourless | 9.0–11 mg/mL | 6.5–7.0 |
| ° C. | Initial | Complies | 10.6 mg/mL | 6.70 |
| 30 | 1 | Complies | 10.8 mg/mL | 6.9 |
| 40 | 1 | Complies | 10.6 mg/mL | 6.8 |
| 50 | 1 | Complies | 10.5 mg/mL | 6.8 |
| 30 | 2 | Complies | 10.7 mg/mL | 6.8 |
| 40 | 2 | Complies | 10.7 mg/mL | 6.6 |
| 50 | 2 | Complies | 10.5 mg/mL | 6.6 |
| 30 | 3 | Complies | 10.4 mg/mL | 6.7 |
| 40 | 3 | Complies | 10.4 mg/mL | 6.7 |
| 50 | 3 | Complies | 10.5 mg/mL | 6.7 |
| 30 | 6 | Complies | 10.5 mg/mL | 6.6 |
| 40 | 6 | Complies | 10.5 mg/mL | 6.6 |
| 50 | 6 | Complies | 10.2 mg/mL | 6.8 |
| 30 | 12 | Complies | 10.5 mg/mL | 6.6 |
| 40 | 12 | Complies | 10.8 mg/mL | 6.6 |

TABLE 2-continued

| TEST | | | | |
|---|---|---|---|---|
| STORAGE CONDITION | TIME (Mths) | Appearance of the solution | Alfaxalone | pH |
| 50 | 12 | Complies | 10.7 mg/mL | 6.6 |
| 30 | 15 | Complies | 10.8 mg/mL | 6.6 |
| 40 | 15 | Complies | 10.6 mg/mL | 6.6 |
| 50 | 15 | Complies | 9.6 mg/mL | 6.6 |

Conclusion:

The product is stable for 15 months at 30° C., 40° C. and 50° C. which indicates that the product would have an expected shelf life of at least 30 months if stored at 30° C. or lower.

Clinical Evaluation

A trial was undertaken to evaluate the efficacy of a composition of the invention in a group of 42 cats. The composition used was a sterile solution of Alfaxalone:HPCD diluted in citro-phosphate buffer pH 6.5 (BP 1998) containing the equivalence of 10 mg/mL alfaxalone.

A summary of the dose range used, route of administration, mean recovery time to head lift and sternal recumbency after anaesthesia and mean surgery time is presented in Table 3.

The mean dose of alfaxalone, where alfaxalone was used as the sole anaesthetic, was 4.5 mg/kg for induction and a mean total dose of 5.8 mg/kg bodyweight. The mean recovery time was 30 minutes to head lift and 44 minutes to sternal recumbency. The mean procedure time was 9 minutes.

Cats ranged in age from 2 months to 16 years of age.

TABLE 3

Use of Alfaxalone:HPCD sterile Injection in cats

| Total Dose Range | Suppl. | | Dose (mg/kg) | | Mean Time (min) | | | Number of |
|---|---|---|---|---|---|---|---|---|
| mg/kg | Dose | Route | Induce | Total | Head Lift | Sternal | Surgery | Observations |
| 0–4.9 | no | I/v | 3.8 | 3.8 | 21 | 27 | 5 | 13 |
| 0–4.9 | yes | I/v and I/v | 2.3 | 3.7 | 38 | 48 | 11 | 3 |
| 0–4.9 | gas | I/v and gas | 3.4 | 3.4 | 35 | 43 | 34 | 7 |
| 5.0–7.5 | no | I/v | 4.6 | 5.8 | 16 | 30 | 6 | 3 |
| 5.0–7.5 | yes | I/v and I/v | 3.3 | 6.4 | 35 | 60 | 19 | 6 |
| 5.0–7.5 | gas | I/v and gas | 7.2 | 7.2 | 13 | 20 | 23 | 4 |
| 7.6–10.0 | no | I/v | 8.3 | 8.3 | 45 | 60 | 5 | 1 |
| 7.6–10.0 | no | I/m | 8.6 | 8.6 | 60 | 85 | 5 | 1 |
| 7.6–10.0 | gas | I/m and gas | 10.0 | 10.0 | ns | ns | ns | 1 |
| 7.6–10.0 | yes | I/m and I/v | 7.5 | 10.0 | 95 | 110 | 5 | 1 |
| >10.0 | yes | I/v and I/v | 10.0 | 16.7 | 35 | 80 | 14 | 2 |
| Summary Alfaxalone Only Doses | | | 4.5 | 5.8 | 30 | 44 | 9 | |

*ns = not specified

Procedures performed under anaesthesia included:

| Abscess | 3 cases |
|---|---|
| Amputation | 1 case |
| Castration | 20 cases |
| Castration/3$^{rd}$ eyelid flap | 1 case |
| Spey | 8 cases |
| Spey/pyometra | 1 case |
| Eye ablation | 1 case |
| Removal of cast | 1 case |
| Dental procedures | 2 cases |
| Lung biopsy | 1 case |
| Tumour removal | 1 case |
| Suture wounds | 2 cases |

Four of the 42 cats were reported to be "jumpy on recovery", one cat vomited on recovery and one cat had a prolonged time to head lift but was then on its feet shortly after lifting its head.

These results clearly indicate that the compositions of the invention are clinically efficacious.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. A stable anaesthetic composition which comprises an aqueous solution of an anaesthetically effective amount of a water soluble cyclodextrin or a cyclodextrin derivative complex of alfaxalone and a citro-phosphate buffer, said buffer having a pH of 6.5,
   wherein
     crystalline material does not form in the composition within about 7 days when stored at 40° C.;
     the water soluble cyclodextrin or cyclodextrin derivative is 2-hydroxypropyl beta-cyclodextrin; and
     the concentration of alfaxalone is 7-15 mg/mL.

2. A sterile ready-to-use dosage of an anaesthetic comprising a package which includes an anaesthetic composition as claimed in claim 1 and one or more antimicrobial agents.

3. A sterile dosage of an anaesthetic composition comprising
   a first package containing in dry form,
     an anaesthetically effective amount of a water soluble cyclodextrin or a cyclodextrin derivative complex of alfaxalone and a citro-phosphate buffer, and
   a second package of sterile water,
   the buffer being selected such that a solution formed by dissolving the contents of the first package with contents of the second package has a pH of 6.5,
   wherein
     crystalline material does not form in the composition within about 7 days when stored at 40° C.;
     the water soluble cyclodextrin or cyclodextrin derivative is 2-hydroxypropyl beta-cyclodextrin; and
     the concentration of alfaxalone is 7-15 mq/mL in the solution formed by dissolving the contents of the first package with contents of the second package.

4. A sterile dosage of an anaesthetic composition comprising
a first package containing in dry form,
an anaesthetically effective amount of a water soluble cyclodextrin or a cyclodextrin derivative complex of alfaxalone, and
a second package containing a sterile aqueous solution of a citro-phosphate buffer,
the buffer being selected such that a solution formed by dissolving the contents of the first package with contents of the second package has a pH of 6.5,
wherein
crystalline material does not form in the composition within about 7 days when stored at 40° C.;
the water soluble cyclodextrin or cyclodextrin derivative is 2-hydroxypropyl beta-cyclodextrin; and
the concentration of alfaxalone is 7-15 mg/mL in the solution formed by dissolving the contents of the first package with contents of the second package.

5. A sterile dosage of an anaesthetic composition comprising a package containing in dry form for reconstitution with sterile water,
an anaesthetically effective amount of a water soluble cyclodextrin or a cyclodextrin derivative complex of alfaxalone and
a citro-phosphate buffer, the buffer being selected such that a solution formed by dissolving the contents of the package with sterile water has a pH of 6.5,
wherein
crystalline material does not form in the composition within about 7 days when stored at 40° C.;
the water soluble cyclodextrin or cyclodextrin derivative is 2-hydroxypropyl beta-cvclodextrin; and
the concentration of alfaxalone is 7-15 mg/mL in the solution formed by dissolving the contents of the first package with contents of the second package.

6. A method of anaesthetising warm-blooded animals comprising administering to said animals an anaesthetically effective amount of a composition as claimed in claim 1.

7. A method of anaesthetising warm-blooded animals comprising administering to said animals an anaesthetically effective amount of the dosage of claim 2.

8. A method as in claim 6 or claim 7 wherein the animal is a dog or a cat.

9. An anaesthetic composition according to claim 1 consisting essentially of an aqueous solution of an anaesthetically effective amount of the water soluble cyclodextrin or a cyclodextrin derivative complex of alfaxalone and a citro-phosphate buffer, said buffer having a pH of 6.5.

10. A sterile dosage of an anaesthetic composition as claimed in claim 3 wherein said first package consists essentially of in dry form, an anaesthetically effective amount of the water soluble cyclodextrin or cyclodextrin derivative complex of alfaxalone and a citro-phosphate buffer, the buffer being selected such that a solution formed by dissolving the contents of the first package with contents of the second package has a pH of 6.5.

11. A sterile dosage of an anaesthetic composition as claimed in claim 4 wherein said first package consists essentially of in dry form, an anaesthetically effective amount of the water soluble cyclodextrin or cyclodextrin derivative complex of alfaxalone, and wherein said second package consists essentially of a sterile aqueous solution of a citro-phosphate buffer, the buffer being selected such that a solution formed by dissolving the contents of the first package with contents of the second package has a pH of 6.5.

12. A sterile dosage of an anaesthetic composition as claimed in claim 5 wherein said package consists essentially of in dry form for reconstitution with sterile water, an anaesthetically effective amount of the water soluble cyclodextrin or cyclodextrin derivative complex of alfaxalone and a citro-phosphate buffer, the buffer being selected such that a solution formed by dissolving the contents of the package with sterile water has a pH of 6.5.

* * * * *